US00PP15307P2

(12) United States Plant Patent
Osada

(10) Patent No.: US PP15,307 P2
(45) Date of Patent: Nov. 9, 2004

(54) ***TILLANDSIA* PLANT NAMED 'TILSTSIL'**

(50) Latin Name: *Tillandsia stricta*
Varietal Denomination: Tilstsil

(76) Inventor: Ken Osada, 3-3 Miyamae-cho, Numazu, Shizuoka (JP), 410-0062

( * ) Notice: Subject to any disclaimer, the term of this patent is extended or adjusted under 35 U.S.C. 154(b) by 0 days.

(21) Appl. No.: 10/704,773

(22) Filed: Nov. 10, 2003

(30) Foreign Application Priority Data

Jan. 14, 2003 (JP) ..... PBR 15406

(51) Int. Cl.[7] ..... A01H 5/00

(52) U.S. Cl. ..... Plt./370

(58) Field of Search ..... Plt./370, 330

*Primary Examiner*—Kent Bell
(74) *Attorney, Agent, or Firm*—Mark P. Bourgeois

(57) ABSTRACT

A new cultivar of *Tillandsia* plant named 'Tilstsil' that is characterized by a fast growth rate of 1 cm every 2 months, large flowers and regular spontaneous flowering. In combination, these traits set 'Tilstsil' apart from other existing varieties of *Tillandsia known to the inventor.*

2 Drawing Sheets

Botanical classification: *Tillandsia stricta.*
Variety denomination: 'Tilstsil'.

BACKGROUND OF THE INVENTION

The present invention relates to a new and distinct cultivar of *Tillandsia* plant botanically known as *Tillandsia stricta* and hereinafter referred to by the cultivar name 'Tilstsil'.

The new cultivar was discovered by the inventor in a cultivated area of Shizuoka, Japan in December of 1988. 'Tilstsil' was discovered as a naturally occurring branch mutation of an unidentified plant of *Tillandsia stricta.*

Asexual reproduction by division of the new cultivar 'Tilstsil' was taken in December of 1998 in Shizuoka, Japan by the inventor. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Tillandsia* cultivar 'Tilstsil'. These traits in combination distinguish 'Tilstsil' as a new and distinct cultivar apart from other existing varieties of *Tillandsia.*

1. *Tillandsia* 'Tilstsil' has a fast growth rate of 1 cm every 2 months.
2. *Tillandsia* 'Tilstsil' exhibits large flowers.
3. *Tillandsia* 'Tilstsil' exhibits regular spontaneous flowering.

The closest comparison variety is *Tillandsia* 'Cotton Candy' (not patented). 'Tilstsil' is different than 'Cotton Candy' in having thinner darker leaves with a softer texture and in producing pups yearly. The surface of *Tillandsia* 'Cotton Candy' leaves have bromeliad scales while 'Tilstsil' does not.

The new cultivar 'Tilstsil' is distinguishable from the parent *Tillandsia* by the following characteristics:

1. 'Tilstsil' has larger flowers.
2. 'Tilstsil' has a faster growth rate.
3. 'Tilstsil' has regular spontaneous flowering.

BRIEF DESCRIPTION OF THE DRAWINGS

The accompanying photographs illustrate the distinguishing traits of *Tillandsia* 'Tilstsil'.

The plant in the first photograph shows an overall view of a 1 year old plant.

The second photograph is a comparison showing an unidentified *Tillandsia* on the left, *Tillandsia* 'Tilstsil' in the middle and *Tillandsia* 'Cotton Candy' on the right. The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Tillandsia* cultivar named 'Tilstsil'. Data was collected in Shizuoka, Japan from 1 year old plastic greenhouse grown plants. The time of year was Winter. The temperatures averaged 25° Centigrade during the day and 20° Centigrade at night in the Summer. In the winter, the daytime temperatures averaged 20° Centigrade and 10° Centigrade at night. The light level was natural outdoor light with 50 percent shade and there were no photoperiodic treatments. Color determinations are in accordance with The Royal Horticultural Society Colour Chart 2001 edition, except where general color terms of ordinary dictionary significance are used. The growing requirements are similar to the species.

'Tilstsil' has not been tested under all possible conditions and phenotypic differences may be observed with variations in environmental, climatic, and cultural conditions, however, without any variance in genotype.

Botanical classification: *Tillandsia stricta.*
Use: Ornamental perennial.
Plant Type: Epiphytic Shrub.
Parentage: 'Tilstsil' was discovered as a naturally occurring branch mutation of an unidentified plant of *Tillandsia stricta.*
Vigor: Medium.
Growth rate: Approximately 1 cm. every 2 months.

Growth habit: Open upright.
Plant shape: Rosette.
Suitable container: 10 cm diameter open mesh shelf, unpotted.
Height: 7 cm. in height.
Width: 12 cm. in width.
Hardiness: USDA Zone 9, withstands light frost.
Propagation: Division.
Crop time: From a division, approximately 1 year is required to produce a finished plant.
Roots:
*Root structure.*—Epiphytic with velamen.
*Root length.*—6.2 cm.
*Individual root diameter.*—0.05 cm.
*Root texture.*—Smooth.
*Root color.*—199C.
Stem: None.
Foliage:
*Texture.*—Rough both sides.
*Leaf arrangement.*—Spiral.
*Compound or single.*—Single.
*Quantity of leaves.*—27.
*Leaf shape.*—Lanceolate, curled.
*Leaf apex.*—Acuminate.
*Leaf base.*—Sessile.
*Leaf length.*—9.8 cm. in length.
*Leaf width.*—0.2 cm. in width.
*Pubescence.*—present on both surfaces toward base.
*Leaf margin.*—Entire, curled.
*Vein pattern.*—Parallel.
*Young leaf color* (*lower surface*).—137A.
*Young leaf color* (*upper surface*).—137B.
*Mature leaf color* (*lower surface*).—137C.
*Mature leaf color* (*upper surface*).—137A.
*Vein color* (*lower surface*).—137A.
*Vein color* (*upper surface*).—137C.
*Leaf attachment.*—Sessile.
*Foliage durability to stress.*—Strong.
Inflorescence:
*Inflorescence type.*—Spike.
*Inflorescence height.*—5.1 cm.
*Inflorescence diameter.*—1.7 cm.
*Lastingness of inflorescence.*—Approximately 2 months.
*Quantity of flowers.*—15 per spike.
*Quantity of flowers and buds per plant.*—Approximately 20.
*Flowering season.*—Winter.
*Time to flower.*—4–8 weeks.
*Rate of flower opening.*—Slow.
*Fragrance.*—None.
*Flower type.*—Tricyclic, hermaphroditic.
*Flower bud length.*—0.7 cm. in length.
*Flower bud diameter.*—0.2 cm. in diameter.
*Flower bud shape.*—Ovate.
*Flower bud color.*—83B.
*Flower aspect.*—Upright.
*Flower shape.*—Bell-shaped.
*Flower dimensions.*—0.2 cm. in diameter, and 1.5 cm. in height.
*Flower longevity.*—A few days.
*Petal texture.*—Smooth.
*Petals fused or unfused.*—Unfused.
*Petal arrangement.*—Radial and upright.
*Petal number.*—3.
*Petal margin.*—Entire.
*Petal shape.*—Linear.
*Petal apex.*—Obtuse.
*Petal base.*—Rounded.
*Petal dimensions.*—1.1 cm. in length, 0.2 cm. in width.
*Petal color when opening* (*upper side*).—89D.
*Petal color when opening* (*under side*).—89D.
*Petal color fully open* (*upper side*).—93B.
*Petal color fully open* (*under side*).—93B.
*Petal color fading.*—83B.
*Petaloids.*—Absent.
Self-cleaning or persistent: Persistent.
Sepals:
*Sepal arrangement.*—Radial.
*Sepal number.*—3.
*Sepal color immature* (*upper side*).—128D.
*Sepal color immature* (*under side*).—128D.
*Sepal color mature* (*upper side*).—62C.
*Sepal color mature* (*under side*).—62C.
*Sepal shape.*—Lanceolate.
*Sepal margin.*—Entire.
*Sepal apex.*—Acuminate.
*Sepal base.*—Sessile.
*Sepal dimensions.*—0.8 cm. in length and 0.2 cm. in width.
Calyx:
*Calyx shape.*—Polysepalous, entire.
*Calyx dimensions.*—0.8 cm. in length and 0.25 cm. in diameter.
Bracts:
*Bract quantity.*—1 per flower.
*Bract arrangement.*—Erect to oblique, calyptrate.
*Bract length.*—1.7 cm.
*Bract width.*—0.8 cm.
*Bract shape.*—Ovate.
*Bract base.*—Sessile.
*Bract apex.*—Acuminate.
*Bract surface.*—Rough, sparse pubescence.
*Bract color* (*both sides*).—65A fading to 69D at base.
Peduncle:
*Peduncle dimensions.*—5 cm. in length and 0.2 cm. in diameter.
*Peduncle angle.*—90° to the rosette, then curving to 45°.
*Peduncle color.*—145B.
*Peduncle strength.*—Weak.
Reproduction organs:
*Stamen number.*—6.
*Anther shape.*—Filantherous.
*Anther dimensions.*—0.15 cm. in length.
*Anther color.*—8D.
*Amount of pollen.*—Moderate.
*Pollen color.*—1D.
*Pistil number.*—1.
*Pistil length.*—0.4 cm.
*Stigma shape.*—Truncate.
*Stigma color.*—9D.
*Style length.*—0.1 cm.
*Style color.*—4D.
*Ovary color.*—145C.
Seed: Seed production has not been observed.
Disease Resistance: Typical of the species.
Pest Resistance: Plants of the new *Tillandsia* have not been observed for pest resistance.

I claim:

1. A new and distinct variety of *Tillandsia* plant named 'Tilstsil' as described and illustrated.

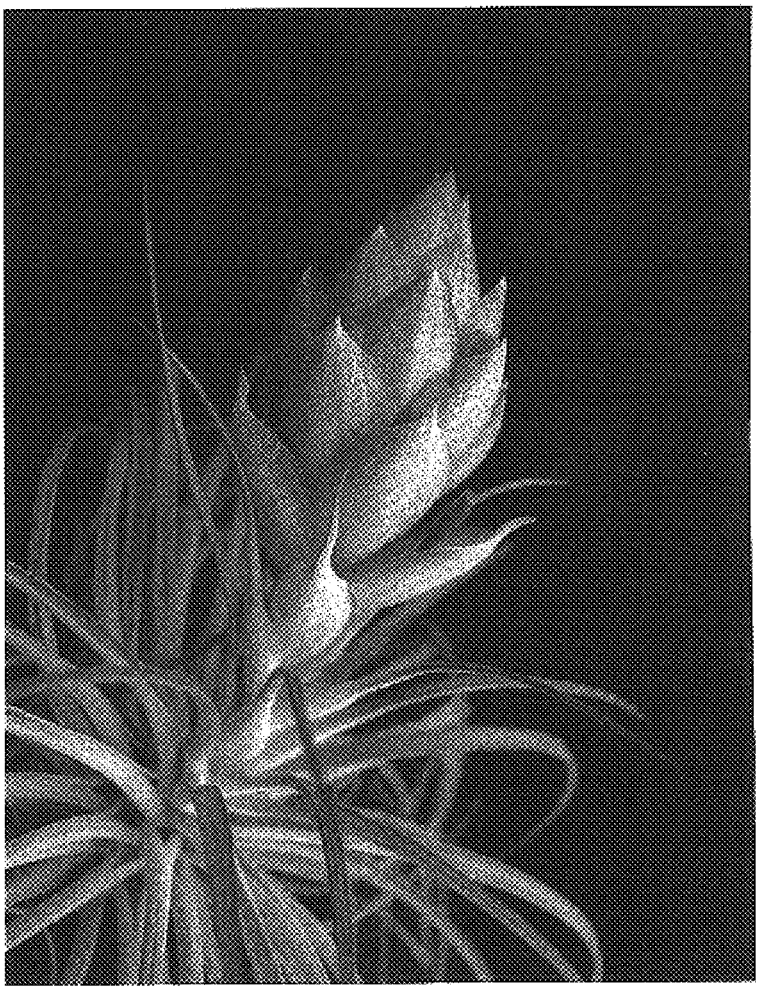

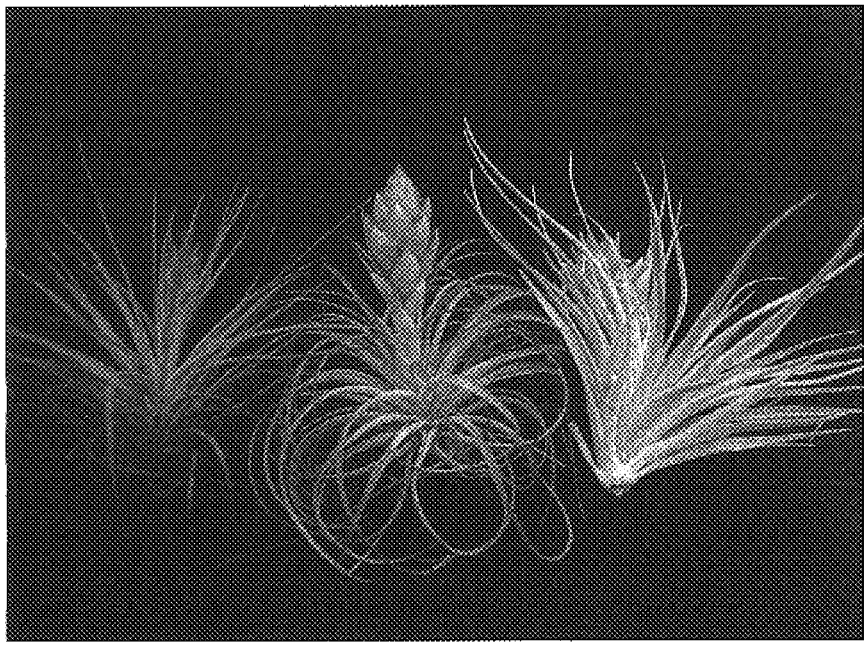

* * * * *